US00PP29344P3

(12) United States Plant Patent
Hennen

(10) Patent No.: US PP29,344 P3
(45) Date of Patent: May 29, 2018

(54) ***PHILODENDRON* PLANT NAMED 'PHM1'**

(50) Latin Name: *Philodendron selloum*
Varietal Denomination: PHM1

(71) Applicant: Gary Hennen, Altha, FL (US)

(72) Inventor: Gary Hennen, Altha, FL (US)

(73) Assignee: Oglesby Plants Int'l. Inc., Altha, FL (US)

( * ) Notice: Subject to any disclaimer, the term of this patent is extended or adjusted under 35 U.S.C. 154(b) by 0 days. days.

(21) Appl. No.: 15/330,311

(22) Filed: Sep. 2, 2016

(65) Prior Publication Data

US 2018/0070519 P1 Mar. 8, 2018

(51) Int. Cl.
*A01H 5/12* (2018.01)

(52) U.S. Cl.
USPC ..... Plt./381
CPC ..... *A01H 5/12* (2013.01)

(58) Field of Classification Search
USPC ..... Plt./381
See application file for complete search history.

*Primary Examiner* — Susan McCormick Ewoldt
(74) *Attorney, Agent, or Firm* — Cassandra Bright

(57) ABSTRACT

A new and distinct *Philodendron* cultivar named 'PHM1' is disclosed, characterized by deeply lobed, glossy, dark green foliage and a distinctive outwardly growing, semi-horizontal habit. Plants grow rapidly and produce an abundance of foliage. Plant habit is well suited for 8 to 12 inch commercial pots. The new variety is a *Philodendron*, normally produced as an indoor ornamental container plant.

1 Drawing Sheet

Latin name of the genus and species: *Philodendron selloum.*

Variety denomination: 'PHM1'.

BACKGROUND OF THE INVENTION

The new *Philodendron* cultivar is a product of chance discovery by the inventor, Gary Hennen, a citizen of the United States. The discovery resulting in this new variety was made September 2010, by Gary Hennen at a commercial nursery in Altha, Fla.

The parent is the unpatented variety *Philodendron selloum* 'Hope'. The new variety was discovered as a naturally occurring whole plant mutation among a population of tissue culture propagated plants used for commercial production of the parent variety.

First asexual reproduction of the new cultivar 'PHM1' was performed by tissue culture at a commercial laboratory in Altha, Fla. in June 2012. Multiple generations have been produced, and have shown that the unique features of this cultivar are stable and reproduced true to type in successive generations.

SUMMARY OF THE INVENTION

The cultivar 'PHM1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PHM1' These characteristics in combination distinguish 'PHM1' as a new and distinct *Philodendron* cultivar:

1. Large dark green mature leaves with a very glossy appearance.
2. Rapid growth.
3. Abundant leaf production.

4. Semi-horizontal growth habit, forming an outwardly spreading plant.
5. Plant habit suitable for 8 to 12 inch commercial pots.
6. Deeply lobed leaf blades.

PARENT COMPARISON

Plants of the new cultivar 'PHM1' are comparable to the parent *Philodendron selloum* 'Hope', unpatented. The two *Philodendron* varieties are similar in most horticultural characteristics however, the new variety 'PHM1' differs in the following:

1. The new variety grows more vigorously than the parent variety.
2. The new variety produces larger foliage, on average 46 cm long and 48 cm wide, compared to 35 cm long and 40 cm wide leaf blades of a similar aged plant of the parent variety.
3. Leaf color of the new variety is Green 139A, parent variety leaf color is Green 137A.
4. Average petiole length of the new variety is 45 to 50 cm, compared to 60 to 70 cm of the parent variety.
5. The new variety is a denser, fuller plant, the parent variety is more open.
6. The leaf petiole, midrib and veins of the new variety are dark green, compared to yellow-Green coloration of similar parts of the parent variety.
7. Average mature plant height of the new variety is 1.2 meters, compared to an average mature height of 1.5 to 1.8 meters of 'Hope'.

COMMERCIAL COMPARISON

Plants of the new cultivar 'PHM1' are comparable to the variety *Philodendron selloum* 'Winterbourne', U.S. Plant Pat. No. 7,030. The two *Philodendron* varieties are similar in most horticultural characteristics however, the new variety 'PHM1' differs in the following:

1. Mature height of the new variety is 1.2 meter, compared to 60 to 90 cm mature height of 'Winterbourne'.
2. The new variety does not produces a red flushing along the veins, as seen on 'Winterbourne'.
3. Foliage of the new variety is not as deeply lobed as that of 'Winterbourne'.
4. The new variety has a wider leaf blade by an average of 8 to 12 cm.

Plants of the new cultivar 'PHM1' are comparable to the commercial variety *Philodendron selloum* 'Twyph0007' U.S. Plant Pat. No. 19,214. The two *Philodendron* varieties are similar in most horticultural characteristics, however the new variety differs in the following:

1. Mature height of the new variety is 1.2 meter, compared to 70 to 90 cm mature height of 'Twyph0007'.
2. The new variety is a fuller, denser plant than 'Twyph0007'.
3. The new variety has a longer leaf blade by an average of 20 cm.
4. The new variety has a wider leaf blade by an average of 25 to 35 cm.
5. The leaf petiole, midrib and veins of the new variety are dark green, compared to Yellow-Green coloration of similar parts of the variety 'Twyph0007'.
6. Leaf margin of the new variety are not as deeply lobed, as leaf margins of 'Twyph0007'.
7. The new variety has a semi-horizontal habit, compared to the upright habit of 'Twyph0007'.

Plants of the new cultivar 'PHM1' are comparable to the commercial variety *Philodendron selloum* 'Little Hope', U.S. Plant Pat. No. 26,282. The two *Philodendron* varieties are similar in most horticultural characteristics, however the new variety differs in the following:

1. Petiole color of the new variety is Green, petiole color of 'Little Hope' is Yellow-Green.
2. Venation color of the new variety is Green, venation color of 'Little Hope' is Yellow-Green.
3. The new variety has a longer leaf blade by an average of 20 cm.
4. The new variety has a wider leaf blade by an average of 20 to 25 cm.

BRIEF DESCRIPTION OF THE PHOTOGRAPH

FIG. 1 illustrates in full color a plant of 'PhM1' in a 10 inch pot, approximately 8 months old from a single rooted tissue culture plantlet. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'PHM1' plants grown in a climate controlled greenhouse in Altha, Fla., USA. Temperatures ranged from 20° C. to 25° C. at night to 25° C. to 32° C. during the day. Light intensity was between 2500 and 3500 foot-candles. No artificial light, photoperiodic treatments were given to the plants. Measurements and numerical values represent averages of typical plant types.

Botanical classification: *Philodendron selloum* 'PHM1'.

Propagation:

*Time to initiate roots.*—About 14 days at approximately 25° C.

*Time to produce a rooted plantlet.*—Approximately 8 to 12 weeks at approximately 22° to 25° C.

*Root description.*—Fleshy, thick, roots covered in fine lateral roots. Colored near RHS White 155A.

Plant:

*Age of the plant described.*—Approximately 8 months from a single rooted tissue culture plantlet.

*Growth habit.*—Semi-horizontal, outwardly spreading, tender tropical.

*Height.*—Approximately 72 cm.

*Plant spread.*—Approximately 137 cm.

*Growth rate.*—Moderate.

*Branching characteristics.*—Approximately 50% of branching is basal. With maturity additional branches occur on higher growing points.

*Number of leaves per stem.*—Approximately 10.

*Length of stem.*—21 cm.

*Diameter of stem.*—1.4 cm.

*Characteristics of stem.*—Form: Round. Color: Near RHS Greyed-Brown 199B. Texture: Glabrous. Oldest part of stem is rough with a somewhat woody texture. Strength: Very strong.

*Internode length.*—1.8 cm to 3.0 cm.

Foliage:

*Arrangement.*—Alternate or irregular spiral. Average Length: Approximately 42 to 46 cm. Average Width: Approximately 45 to 50 cm at widest point. Shape of blade: Highly lobed, overall oblate. Apex: Acute. Base: Cordate. Margin: Undulating and deeply lobed. Aspect: Recurved downward, slightly undulate. Texture of top surface: Glabrous. Texture of bottom surface: Glabrous. Appearance of top surface: Very glossy. Appearance of lower surface: Slightly shiny. Color: Young foliage upper side: Near RHS Green 139A. Young foliage under side: Near RHS Green 137B. Mature foliage upper side: Near RHS Green 139A. Mature foliage under side: Near RHS Green 137A. Venation: Type: Palmate. Midrib characteristics: Protruding very slightly on upperside, significantly on underside. Venation coloration: Mid rib upperside: Near RHS Green 137B. Mid rib underside: Near RHS Green 143B. Lateral veins upperside: Near RHS Green 137B. Lateral veins underside: Near RHS Green 141D. Lobes: Quantity: Average range 8 to 16 lobes per leaf. Length from mid rib vein to apex: Average range 22 cm to 29 cm. Width: Average range 3.2 to 4.0 cm. Shape: Narrowly oblong. Aspect: Straight to undulate. Margin: Highly undulating, nearly ruffled. Entire.

*Petiole.*—Length: Average range for mature leaf 45 to 55 cm. Width: At base 1.3 cm near leaf blade 0.9 cm. Color Upperside: Near RHS Green 137B. Underside: Between RHS Green 141B and 141C. Angle: Approximately 30° angle to stem. Older foliage approximately 60° to 75° to stem. Strength: Very strong, moderately flexible. Texture: Very slightly ribbed texture. Glabrous.

Flower: Flowering has not been observed.

Other characteristics:

*Disease/pest resistance.*—Neither resistance nor susceptibility to pathogens and pests common to *Philodendron* have been observed.

*Temperature tolerance.*—The new variety tolerates temperatures between −2 to 40° C.

*Fruit/seed production.*—Not observed.

What is claimed is:

1. A new and distinct cultivar of *Philodendron* plant named 'PHM1' as herein illustrated and described.

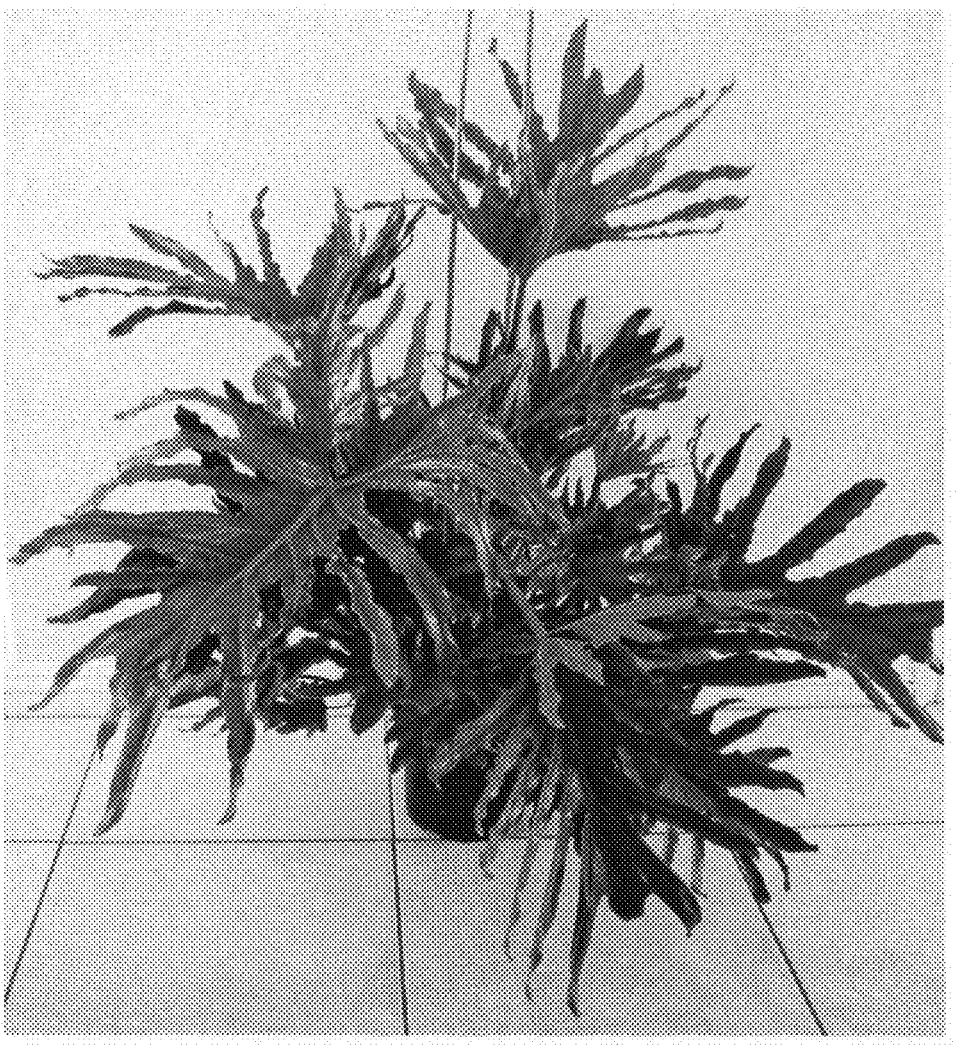

* * * * *